United States Patent
Stamler

[19]

[11] Patent Number: 6,034,293
[45] Date of Patent: Mar. 7, 2000

[54] EYELID SPLINT

[76] Inventor: John F. Stamler, 346 Ferson Ave., Iowa City, Iowa 52446

[21] Appl. No.: 08/955,143

[22] Filed: Oct. 21, 1997

[51] Int. Cl.⁷ ............................... A61F 13/00; A61F 9/00
[52] U.S. Cl. .............................................. 602/41; 128/858
[58] Field of Search ........................... 602/41, 54, 57–59; 206/460, 461; 128/892, 893, 858

[56] References Cited

U.S. PATENT DOCUMENTS

| | | | |
|---|---|---|---|
| 3,548,420 | 12/1970 | Spence | 128/892 X |
| 3,619,815 | 11/1971 | Towner, Jr. | 3/12 |
| 4,134,401 | 1/1979 | Galician | 128/163 |
| 4,599,746 | 7/1986 | Stoner | 2/15 |
| 4,649,908 | 3/1987 | Ghaly | 128/132 |
| 4,653,483 | 3/1987 | Clavin | 128/76.5 |
| 4,677,974 | 7/1987 | Leonardi | 128/163 |
| 4,732,808 | 3/1988 | Krampe et al. | 428/355 |
| 4,787,380 | 11/1988 | Scott | 602/57 X |
| 4,854,307 | 8/1989 | Elfenbein | 128/76.5 |
| 4,906,240 | 3/1990 | Reed et al. | 602/46 X |
| 4,917,112 | 4/1990 | Kalt | 602/58 |
| 5,000,172 | 3/1991 | Ward | 602/52 |
| 5,144,944 | 9/1992 | Rice | 602/74 |
| 5,180,360 | 1/1993 | Rhame, Jr. | 602/74 |
| 5,336,219 | 8/1994 | Krantz | 606/215 |
| 5,389,066 | 2/1995 | Rhame, Jr. | 602/74 |
| 5,547,465 | 8/1996 | Powell | 602/54 |

*Primary Examiner*—Richard J. Apley
*Assistant Examiner*—Denise Pothier
*Attorney, Agent, or Firm*—David P. Gordon; David S. Jacobson; Thomas A. Gallagher

[57] ABSTRACT

An eyelid splint for immobilizing the upper lid of an eye in a closed position includes a substantially rigid member, an adhesive applied to the back of the substantially rigid member, and a peel-off backing covering the adhesive. The substantially rigid member, by definition, resists folding or severe bending when adhered to the upper lid. The substantially rigid member is provided with the general shape and size of an upper lid in a closed position, and includes a removal tab. According to a preferred embodiment, the substantially rigid member is made from a medical grade polyethylene, plastic, vinyl, or silastic material, preferably porous and having high oxygen permeability. The removal tab is preferably provided on the superior edge of the eyelid splint and is preferably includes no adhesive backing. The inferior edge of the eyelid splint is contoured to the general shape of the lower edge of the upper lid. The substantially rigid member, when adhered to the upper lid by the adhesive comfortably immobilizes the upper lid in a closed position. In addition, the eyelid splint is not bulky and is transparent, and therefore is practically unnoticeable to a casual observer. Therefore the eyelid splint of the invention is more acceptable to a patient. Moreover, without removing the eyelid splint, access to the eye for application of medication and examination is easily provided.

19 Claims, 4 Drawing Sheets

EYELID SPLINT

BACKGROUND OF THE INVENTION

1. Field of the Invention

This invention relates broadly to eye bandages. More particularly, this invention relates to a post-operative eyelid splint which maintains the upper lid in a closed position.

2. State of the Art

Frequently after eye surgery or eye injury, the upper lid must be maintained in a closed position over the eye. A closed upper lid aids healing following corneal or cataract surgery. In addition, recovery from conditions such as corneal abrasions, corneal ulcers, corneal burns, and keratitis is helped from the constant protection offered by fixing the upper and lower lids relative to each other, i.e., in a closed position.

One method of immobilizing the eyelids is tarsorrhaphy; that is, suturing the upper and lower eyelids closed. The method is very effective. However, it requires surgery which is painful, expensive, and time consuming. The procedure can also cause scaring at the eyelid margins. Moreover, tarsorrhaphies are cosmetically undesirable.

Another method of protecting the cornea, but which does not immobilize the lids, is the use of a bandage contact lens. Bandage contact lenses easily fit between the eyelids and the cornea. In addition, they are cosmetically acceptable, are relatively inexpensive, and can easily be removed. However, bandage contact lenses often fall out of eyes without patient knowledge and are also prone to causing corneal infections. The fear of infection limits their use to occasional use and only by ophthalmologists. Moreover, the use of bandage contact lenses is limited to particular applications in which it is permissible for the eyelids to move over the cornea and sclera.

The most common method of eyelid immobilization is carried out by placing pressure with a bandage against the upper and lower lids to maintain the upper and lower lids in a closed position. This is most typically done by placing cotton pads over a closed upper lid, and tightly wrapping tape around the cotton pads and the head of the patient to place pressure on, and thereby immobilize, the lid. However, the tight pressure placed by the bandage on the eye can cause discomfort to the patient. As a result, the patient often prematurely removes the bandage, thereby irritating and potentially causing harm to the eye. In addition, a bandage of cotton pads and tape can be very bulky (preventing the use of eyeglasses for the non-bandaged eye) and is also unsightly. Furthermore, each time access to the eye is required, e.g., for examination by a physician or for administration of a medication, the complete bandage must be removed and discarded, and a new bandage must be then be applied. In removing the tape of the bandage from the face, the facial skin is often irritated or abraded.

Because of these problems a number of other eyelid immobilization products have been proposed. For example, U.S. Pat. No. 4,134,401 to Galician discloses an eye patching system which includes a narrow adhesive strip and other optional components. The adhesive strip is provided across the upper and lower lids (i.e., perpendicular to the juncture of the upper and lower lids) to hold the lids together and, thus, immobile. A strip of absorbent material, potentially carrying medicine, may be coupled on one side to a large piece of tape, and the piece of tape may be adhered to the upper and lower lids such that the strip of absorbent material is positioned lengthwise along the juncture of the upper lids. The absorbent material is thus able to supply medicine through the juncture. A gauze sponge may also be applied to the tape between the tape and the absorbent material. The narrow adhesive strip and tape assembly are separate components, applied separately, which presumably work in conjunction with each other. While the Galician device is not nearly as bulky as conventional eye bandages, proper alignment of the separate components requires a high degree of skill. It will be appreciated that the small and narrow adhesive strip must be aligned generally vertically while the strip of absorbent material must be aligned generally horizontally. Moreover, examination of the eye and the administration of medicine (other than that already located on the absorbent strip) requires removal of at least a portion of the bandage.

U.S. Pat. No. 4,677,974 to Leonardi describes another bandage device formed of a foam member coupled to a rigid backing. Rather than using an adhesive to hold the bandage against the eye, the device utilizes two elastic straps having hook and loop fastening means, with each of the elastic straps being coupled to opposite ends of the backing. The foam member is placed against the upper and lower lids and the straps are fastened around the back of the head of a patient. While the bandage device may be applied and removed rather easily, it nevertheless immobilizes the eyelid using pressure, which can cause discomfort to the patient. In addition, the device is rather conspicuous and may cause a patient to be self-conscious about wearing the bandage, potentially to the point of causing the patient to remove the device.

U.S. Pat. Nos. 5,180,360 and 5,389,066 to Rhame, Jr., describe yet another bandage device which includes a foam or inflatable bladder portion which maintains the eyelid in a closed position. A large oval or rectangular adhesive patch, which adheres to the skin around the eye, holds the foam or bladder portion in position against the upper lid. Like other prior art bandages, the device uses pressure against the upper lid to keep the lid closed and the device must be removed to examine or administer medication to the eye.

A more recent method for maintaining the upper eyelid in a closed position uses serrated, transparent, adhesive tape, which is torn into a one-inch by one-inch piece and firmly pressed onto the lid. The tape splints the lid (i.e., stiffens the lid), preventing the lid from being opened when such is attempted by a patient. However, as the tape is relatively thin and transparent, and because the tape has been firmly pressed to the lid, removal of the tape from the lid is difficult. Furthermore, because the torn pieces of tape are rectangular in shape, by nature of the serrations, the tape pieces are not ideally suited to the shape of the upper eyelid which is more oval in shape. Moreover, the adhesive of the tape is relatively weak, causing unintentional detachment of the tape from the lid in approximately twelve to twenty-four hours.

SUMMARY OF THE INVENTION

It is therefore an object of the invention to provide an eyelid splint which can comfortably immobilize the upper lid in a closed position.

It is another object of the invention to provide an eyelid splint which is easy to remove from the upper lid of an eye.

It is also an object of the invention to provide an eyelid splint which is relatively thin and inconspicuous, and ideally shaped for use on the upper lid.

It is a further object of the invention to provide an eyelid splint which can provide access to the eye without removing the splint.

It is an additional object of the invention to provide an eyelid splint which is easy to position on the upper lid.

In accord with these objects, which will be discussed in detail below, an eyelid splint is provided which is generally made from a biocompatible material having generally the shape and size of an upper lid in a closed position. One side of the splint is provided with a medical adhesive and is adherable to the upper lid. A removal tab portion of the eyelid splint preferably extends from the superior edge of the eyelid splint and is preferably provided with no adhesive backing. The material of the eyelid splint is sufficiently rigid such that the eyelid splint comfortably immobilizes the upper lid in a closed position.

According to a preferred embodiment of the invention, the eyelid splint is made from a transparent medical grade plastic or silastic material. Preferably the material chosen has high oxygen permeability. The inferior edge of the eyelid splint is contoured to the general shape of the lower edge of the upper lid. According to other aspects and embodiments of the invention, the inferior edge of the eyelid splint is provided with more adhesive or a stronger adhesive than the remainder of the eyelid splint, a separate removal tab is coupled to the eyelid splint, and the material of the eyelid splint is writable (for medical notation) thereon.

Before applying the eyelid splint to an upper lid, the lid skin is cleaned of oil and moisture with an alcohol swab. The eyelid is then gently closed to remove folds from the skin, and the skin is stretched by pulling down on the lashes of the upper lid (or up on the brow of the eye). The eyelid splint is placed on the skin of the eyelid with the inferior edge positioned just above the lashes. The eyelid splint is then preferably held firmly in place for approximately fifteen to thirty seconds to allow the adhesive along the inferior edge and on the back of the eyelid splint to adhere to the skin of the eyelid. The eyelid splint may easily be removed by holding the skin at the brow, positioning a fingernail behind the eyelid splint at the removal tab, and pulling the eyelid splint down and off the eyelid using the fingernail.

It will be appreciated that because the eyelid splint of the invention does not rely on pressure to maintain the lid in a closed position, the eyelid splint is more comfortable to use than other bandage devices. In addition, the eyelid splint of the invention is not bulky and, due to its transparency, is practically unnoticeable to a casual observer, and therefore more acceptable to a patient. Moreover, with the eyelid splint of the invention, access to the eye is possible by pulling down on the lower lid or by lifting the brow skin upwards without removing the eyelid splint.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
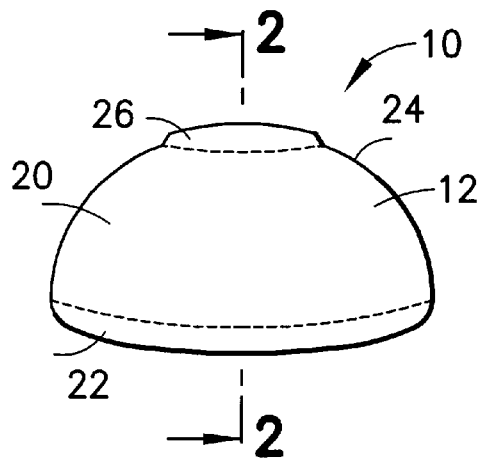
FIG. 1 is a side elevation of a first embodiment of an eyelid splint of the invention.
Figure 2:
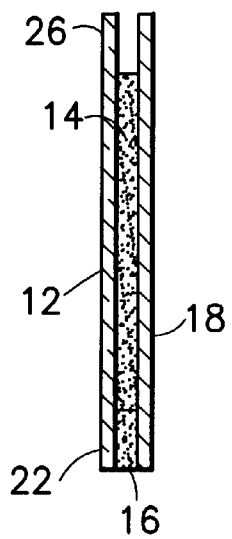
FIG. 2 is a cross-section through line 2—2 in FIG. 1.

Turning now to FIGS. 1 and 2, and according to a preferred embodiment of the invention, an eyelid splint 10 for the upper lid generally includes a substantially rigid member 12, adhesives 14, 16, and a peel-off backing 18. For purposes of the description of the substantially rigid member 12, it will appreciated that "substantially rigid" means that the member 12 resists folding or severe bending when applied to the upper lid, as described below. The substantially rigid member 12 is generally made from a relatively thin layer of biocompatible material. The material is preferably transparent, porous, and oxygen permeable, e.g., a medical grade silastic, polyethylene, cellophane, or plastic material. One preferred material is transparent 3.0 mils medical grade polyethylene. The substantially rigid member 12 is provided with the general shape and size of an upper lid in a closed position; i.e., generally oval. The substantially rigid member 12 has a central portion 20 bounded by an inferior edge 22 and a superior edge 24. The inferior edge 22 of the substantially rigid member 12 is curved to have a contour similar to the contour of the edge of an upper lid. The superior edge 24 is provided with a removal tab 26.

The back of the central portion 20 and inferior edge 22 of the substantially rigid member 12 (and preferably not the removal tab 26) are provided with a medical grade adhesive 14 which is adherable to the skin of the upper lid. Alternatively, two adhesives may be used, a first medical grade adhesive 14 being applied to the central portion 20, and a second stronger medical grade adhesive 16 being applied along the inferior edge 22. As yet another alternative, the same adhesive may be applied to the central portion and inferior edge, with the inferior edge having more adhesive per square centimeter applied thereto. One preferred adhesive is a nonsensitizing acrylic copolymer pressure-sensitive adhesive. The peel-off backing 18 is provided over the adhesives 14, 16. A preferred combination of the biocompatible material and adhesive is similar to one sold under the trademark MED 3044 by Avery Dennison.

By way of example, and not by way of any limitation, the following preferable dimensions for the eyelid splint are provided. The substantially rigid member is approximately 1.5 cm to 2.5 cm from removal tab to inferior edge, and approximately 2.5 cm to 4 cm in width. The inferior edge of the eyelid splint has a radius of curvature of approximately 5 cm to 9 cm. The thickness of the substantially rigid member is approximately 0.05 to 1.5 mm.

Figure 3:
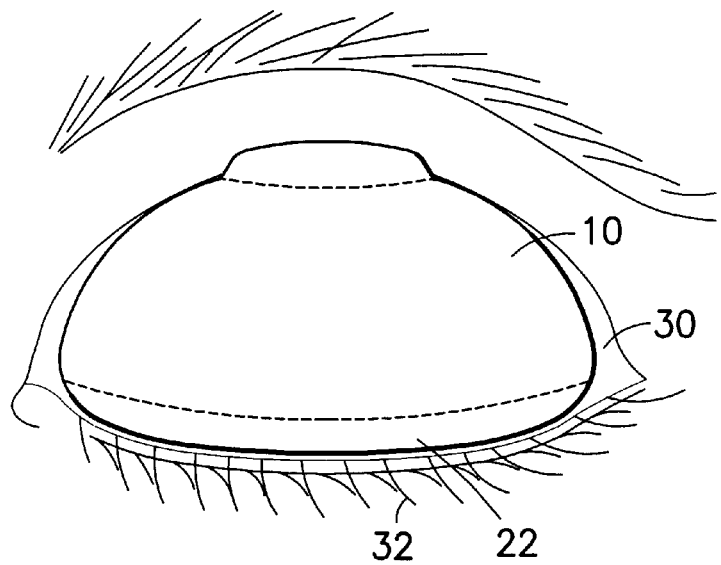
FIG. 3 is an enlarged view of the eyelid splint of FIG. 1, shown positioned on the upper lid of an eye.

Before applying the eyelid splint 10, the eyelid skin is cleaned of oil and moisture with an alcohol swab. The eyelid is then gently closed to remove folds from the skin, and the skin is stretched by pulling down on the lashes of the upper lid (or up on the brow of the eye). Referring to FIG. 3, the eyelid splint 10 is placed on the skin of the eyelid 30 with the inferior edge 22 positioned just above the lashes 32. The eyelid splint is then preferably held firmly in place for approximately fifteen to thirty seconds to allow the adhesives along the inferior edge and on the back of the eyelid splint to adhere to the skin of the eyelid.

Figure 4:
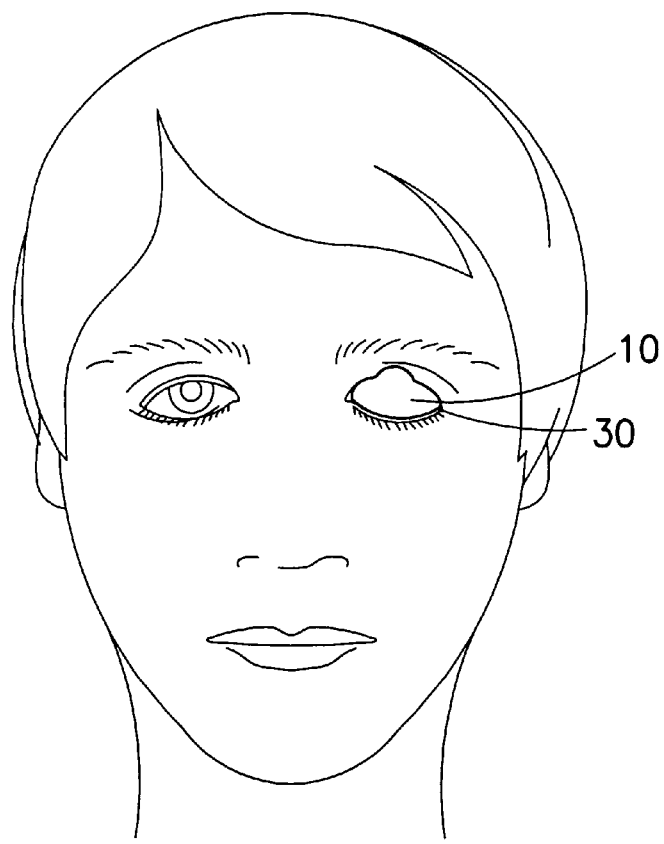
FIG. 4 is a view of a patient wearing an eyelid splint according to the first embodiment of the invention.
Figure 5:
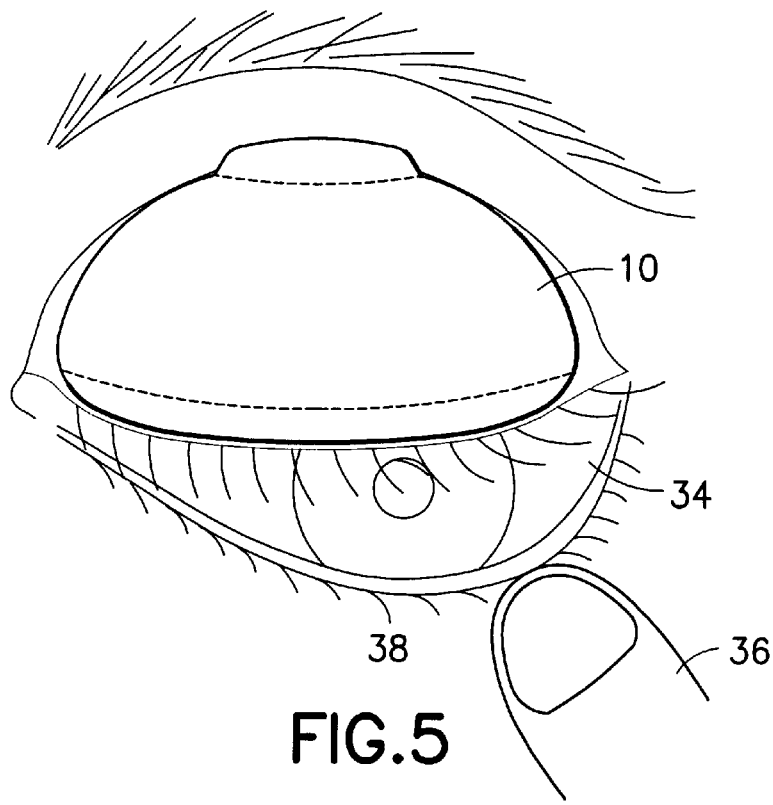
FIGS. 5 and 6 illustrate ways in which access can be provided to an eye having on its upper lid an eyelid splint according to the invention.
Figure 6:
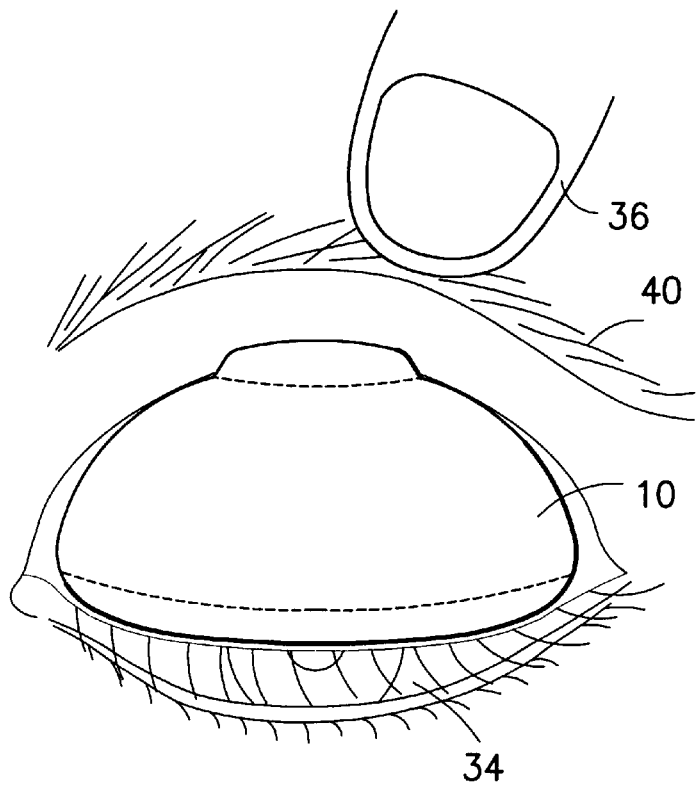
Figure 7:
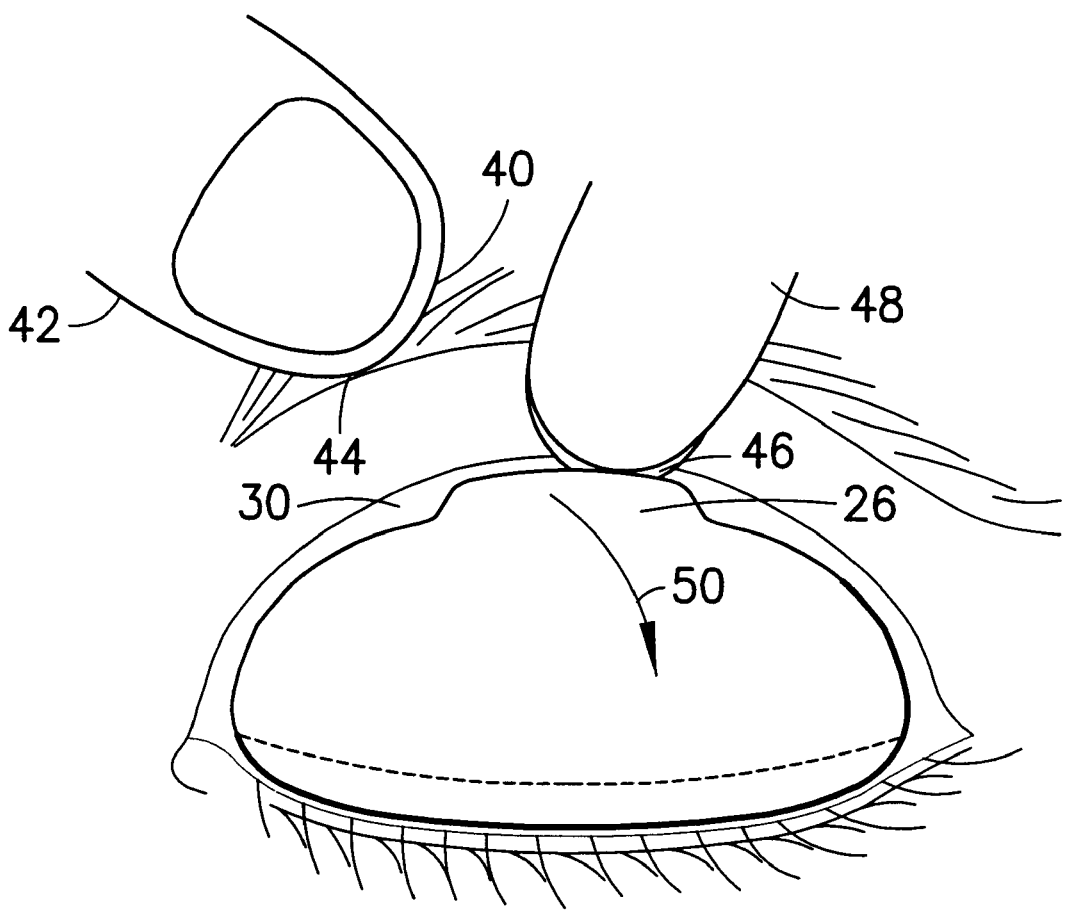
FIG. 7 is illustrates the method of removing the eyelid splint from the upper lid of an eye.

Turning to FIG. 4, the material of the eyelid splint has sufficient rigidity to resist folding such that when the eyelid splint 10 is adhered to the upper lid 30, the upper lid is comfortably immobilized in a closed position. It will be appreciated that because the eyelid splint does not rely on pressure to maintain the lid in a closed position, the eyelid splint is more comfortable to use than other bandage devices. In addition, the eyelid splint is not bulky and is practically unnoticeable to a casual observer. Therefore the eyelid splint of the invention is more acceptable to a patient. Moreover, without removing the eyelid splint 10, the patient can obtain access to the eye 34 for the application of medication by using a finger 36 to pull down on the lower lid 38 (FIG. 5) or lift the brow 40 upwards (FIG. 6). Moreover, by obtaining visual access to the eye in the same manner, the physician can examine the cornea of the eye (by the patient looking downward to position the cornea for examination) without removing the eyelid splint. Referring to FIG. 7, the eyelid splint 10 may easily be removed by using a first finger 42 (e.g, a thumb) to hold the skin 44 at the brow 40, positioning a fingernail 46 of a second finger 48 behind the eyelid splint at the removal tab 26, and using the fingernail 46 to pull the eyelid splint (in the direction of arrow 50) down and off the eyelid 30.

Figure 8:
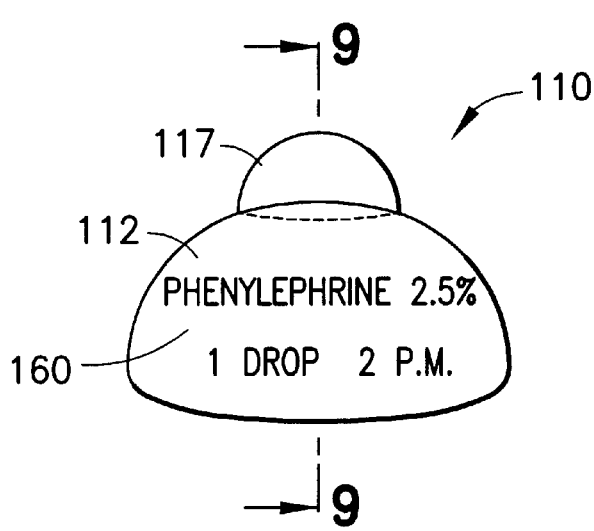
FIG. 8 is a side elevation of a second embodiment of the invention.
Figure 9:
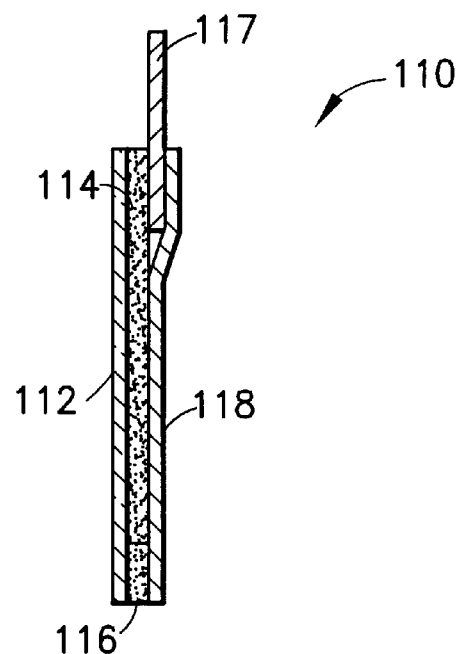
FIG. 9 is a cross-section through line 9—9 in FIG. 8.

Turning now to FIGS. 8 and 9, a second embodiment of an eyelid splint 110, substantially similar to the eyelid splint of the first embodiment (with like parts having numbers incremented by 100) is shown. The eyelid splint 110 generally includes a substantially rigid member 112, adhesives 114, 116, a distinct removal tab 117 and a peel-off backing 118. The substantially rigid member 112 is preferably made from a material which is writable thereon for medical notation 160. The removal tab 117 is coupled to the substantially rigid member 112 via the adhesive 114, and is positioned at the upper portion of the substantially rigid member 112. The removal tab 117 permits the eyelid splint, when applied to the upper lid of an eye, to be removed by simply pulling on the removal tab such that the eyelid splint "peels" away from the upper lid.

There have been described and illustrated herein embodiments of an eyelid splint. While particular embodiments of the invention have been described, it is not intended that the invention be limited thereto, as it is intended that the invention be as broad in scope as the art will allow and that the specification be read likewise. Thus, while particular materials, e.g., polyethylene, cellophane, silastics and plastics, have been disclosed, it will be appreciated that other materials may be used as well. For example, a cling vinyl film as sold under the trademark FLEXMARK® CV-800-C by Flexcon Company of Spencer, Me., may be used which requires no adhesive. In addition, while the material is preferably porous, it will be appreciated that the material may alternatively be non-porous and/or additionally be perforate to permit increased oxygen permeability. Furthermore while the eyelid splint has been shown as having adhesives on the substantially rigid member and a peel-off backing covering the adhesives, it will be appreciated that neither the adhesives nor the backing are required and that the eyelid splint may be applied to the upper lid using a liquid medical grade adhesive. In addition, while the removal tab is preferably provided at the superior edge of the splint, it will be appreciated that the removal tab may be provided elsewhere around the perimeter of the eyelid splint. Moreover, while particular dimensions are provided in the above example it will be appreciated that other dimensions can be used as the eyelid splint may be pre-formed for a variety of eye shapes and sizes, from children to adults. However, it will also be appreciated that the eyelid splint is not necessarily required to be made in a plurality of shapes and sizes, as the eyelid splint may easily be cut to fit almost any eyelid shape and size. It will therefore be appreciated by those skilled in the art that yet other modifications could be made to the provided invention without deviating from its spirit and scope as so claimed.

What is claimed is:

1. An eyelid splint for immobilizing an upper lid of an eye in a closed position, comprising:
    a) a biocompatible substantially rigid member having a back side, an inferior edge having a first radius of curvature of approximately 5 cm to 9 cm, a superior edae having a second radius of curvature smaller than said first radius of curvature, a height of approximately 1.5 cm to 2.5 cm and a width of approximately 2.4 cm to 4 cm;
    b) a first adhesive provided on said back side of the substantially rigid member; and
    c) a peel-off backing provided over said adhesive.

2. An eyelid splint according to claim 1, further comprising:
    d) a removal tab coupled to said substantially rigid member.

3. An eyelid splint according to claim 2, wherein: said substantially rigid member includes a superior edge, and said removal tab is coupled to said superior edge.

4. An eyelid splint according to claim 3, wherein: said removal tab is unitarily formed with said substantially rigid member.

5. An eyelid splint according to claim 1, wherein: said substantially rigid member is made of one of a polyethylene, vinyl, plastic and silastic material.

6. An eyelid splint according to claim 5, wherein: said first adhesive is a nonsensitizing acrylic copolymer.

7. An eyelid splint according to claim 1, wherein: said substantially rigid member is transparent.

8. An eyelid splint according to claim 1, wherein: said substantially rigid member is at least one of porous, perforate, and oxygen permeable.

9. An eyelid splint according to claim 1, wherein: said substantially rigid member is writable thereon.

10. An eyelid splint according to claim 1, wherein: said substantially rigid member has an inferior edge which is provided with a second adhesive which is adhesively stronger than said first adhesive.

11. An eyelid splint according to claim 1, wherein: said substantially rigid member has a thickness of approximately 0.05 to 1.5 mm.

12. An eyelid splint according to claim 1, wherein: said back side includes a center and said first adhesive is provided on said center of said back side.

13. An eyelid splint for immobilizing an upper lid of an eye in a closed position; the upper lid having a lower edge, comprising:
    a) a biocompatible substantially rigid member, an inferior edge having a first radius of curvature of approximately 5 cm to 9 cm, a superior edge having a second radius of curvature smaller than said first radius of curvature, a height of approximately 1.5 cm to 2.5 cm and a width of approximately 2.4 cm to 4 cm; and
    b) first adhesive means for adhering said substantially rigid member to the upper lid.

14. An eyelid splint according to claim 13, wherein: said substantially rigid member has an inferior edge, and said eyelid splint further comprises,
    c) second adhesive means for adhering said inferior edge to the lower edge of the upper lid, said second adhesive being adhesively stronger than said first adhesive.

15. An eyelid splint according to claim 13, further comprising:
   d) removal means for removing said substantially rigid member from the upper lid of the eye after said eyelid splint has been coupled to the upper lid.

16. An eyelid splint according to claim 13, wherein:
   said substantially rigid member includes a back side having a center and said first adhesive means is provided to said center of said back side.

17. An eyelid splint which when coupled to an upper lid of an eye in a closed position immobilizes the eye, said eyelid splint comprising:
   a) a biocompatible substantially rigid member having an inferior edge having a first radius of curvature of approximately 5 cm to 9 cm, a superior edge having a second radius of curvature smaller than said first radius of curvature, a height of approximately 1.5 cm to 2.5 cm and a width of approximately 2.4 cm to 4 cm; and
   b) a removal means coupled to said substantially rigid member for decoupling said eyelid splint from the eye.

18. An eyelid splint according to claim 17, wherein:
   said substantially rigid member is made of one of a polyethylene, vinyl, plastic and silastic material.

19. An eyelid splint according to claim 17, wherein:
   said substantially rigid member is at least one of porous, perforate, and oxygen permeable.

* * * * *